United States Patent [19]

Newman

[11] Patent Number: 5,264,554
[45] Date of Patent: Nov. 23, 1993

[54] PLATELET CELL ADHESION MOLECULE AND VARIANTS THEREOF

[75] Inventor: Peter J. Newman, Shorewood, Wis.

[73] Assignee: The Blood Center of Southeastern Wisconsin, Inc., Milwaukee, Wis.

[21] Appl. No.: 466,140

[22] Filed: Jan. 19, 1990

[51] Int. Cl.$^5$ .................... C07K 13/00; C07K 9/00; C07K 15/14; A61K 39/00

[52] U.S. Cl. .................... 530/387.1; 530/395; 530/350; 530/324; 435/69.1; 424/85.8

[58] Field of Search .............. 530/387, 388, 380, 395, 530/330, 329, 328, 327, 326, 325, 324, 350, 387.1; 514/8, 12; 435/69.1; 424/85.8

[56] References Cited

U.S. PATENT DOCUMENTS

| | | | |
|---|---|---|---|
| 4,456,082 | 6/1984 | Harrison | 175/384 |
| 4,699,880 | 10/1987 | Goldstein | 435/172.2 |
| 4,704,692 | 11/1987 | Ladner | 364/496 |
| 4,806,472 | 2/1989 | de Louvencourt et al. | 435/68 |
| 4,808,537 | 2/1989 | Stroman et al. | 435/6 |
| 4,837,147 | 6/1989 | Oshiman et al. | 435/68 |
| 4,855,231 | 8/1989 | Stroman et al. | 435/68 |
| 4,857,467 | 8/1989 | Sreekrishna et al. | 435/255 |
| 4,859,596 | 8/1989 | Hollenberg et al. | 435/172.3 |
| 5,081,034 | 1/1992 | Bevilaqua et al. | 435/252.33 |

FOREIGN PATENT DOCUMENTS 0330191  8/1989  European Pat. Off. ............ 530/350

OTHER PUBLICATIONS

Albelda, S. et al., The Journal of Cell Biology, 114(5): 1059–1068, Sep. 1991.
Edgell et al., "Permanent Cell Line Expressing Human Factor VIII–Related Antigen Established by Hybridization," Proc. Nat'l. Acad Sci. USA 80:3734–3737 (1983).
Gillies et al., "Expression of Human Anti–Tetanus Toxoid Antibody in Transfected Murine Myeloma Cells," Biotechnol. 7:799–804 (1989).
Goyert et al., "Biochemistry and Expression of Myelomonocytic Antigens," J. Immunol. 137:3909–3914 (1986).
Graham et al., "Characteristics of a Human Cell Line Transformed by DNA from Human Adenovirus Type 5," J. Gen. Virol. 36:59–72 (1977).
Hall et al., "Major Surface Antigen Gene of a Human Malaria Parasite Cloned and Expressed in Bacteria," Nature (London) 311:379–382 (1984).
Hunkapiller et al., "The Growing Immunoglobulin Gene Superfamily," Nature 323:15–16 (1986).
Huse et al., "Generation of a Large Combinatorial Library of the Immunoglobulin Repertoire in Phage Lambda," Science 246:1275–1281 (1989).
Knapp et al., "Towards a Better Definition of Human Leucocyte Surface Molecules," Immunology Today 10:253–258 (1989).
Kozak, "An Analysis of 5'–Noncoding Sequences from 699 Vertebrate Messenger RNAs," Nucleic Acids Res. 15:8125–8148 (1987).
Landegren et al., "A Ligase–Mediated Gene Detection Technique," Science 241:1077–1080 (1988).
Lee et al., "Isolation and Immunocytochemical Characterization of Human Bone Marrow Stromal Macrophages in Hemopoietic Clusters," J. Exp. Med. 168:1193–1198 (1988).
Lipman et al., "Rapid and Sensitive Protein Similarity Searches," Science 227:1435–1441 (1985).
Mather et al., "Culture of Testicular Cells in Hormone–Supplemented Serum–Free Medium," Ann. N.Y. Acad. Sci. 383:44–68 (1982).

(List continued on next page.)

Primary Examiner—Merrell C. Cashion, Jr.
Assistant Examiner—Susan M. Perkins
Attorney, Agent, or Firm—Foley & Lardner

[57] ABSTRACT

A glycoprotein, PECAM-1, and variants thereof can be obtained by expression in a transformed host cell of a polynucleotide coding for the glycoprotein or a variant polypeptide. PECAM-1 can also be isolated from cellular sources. An antibody specific for PECAM-1 or a PECAM variant can be produced via recombinant techniques, or can be obtained from a hybridoma.

4 Claims, 5 Drawing Sheets

OTHER PUBLICATIONS

Mather, "Establishment and Characterization of Two Distinct Mouse Testicular Epithelial Cell Lines," *Biol. Reprod.* 23:243–252 (1980).

Muller et al., "A Human Endothelial Cell-Restricted, Externally Disposed Plasmalemmal Protein Enriched in Intercellular Junctions," *J. Exp. Med.* 170:399–414 (1989).

Nakatani et al., "Functional Expression of Human Monoclonal Antibody Genes Directed Against Pseudomonal Extoxin A in Mouse Myeloma Cells," *Biotechnol.* 7:805–810 (1989).

Newman et al., "Detection and Characterization of Monoclonal Antibodies to Platelet Membrane Proteins," *J. Cell. Biol.* 90:249–253 (1981).

Newman et al., "Synthesis by Cultured Human Umbilical Vein Endothelial Cells of Two Proteins Structurally and Immunologically Related to Platelet Membrane Glycoproteins IIb and IIIa," *J. Cell. Biol.* 103:81–86 (1986).

Newman et al., "Extraction and Identification of Human Platelet Integral Membrane Proteins Using Triton X-114," *Thrombosis Res.* 27:221–224 (1982).

Ohto et al., "A Novel Leukocyte Differentiation Antigen: Two Monoclonal Antibodies TM2 and TM3 Define a 120-kd Molecule Present on Neutrophils, Monocytes, Platelets, and Activated Lymphoblasts," *Blood* 66:873:881 (1985).

Urlaub et al., "Isolation of Chinese Hamster Cell Mutants Deficient in Dihydrofolate Reductase Activity," *Proc. Nat'l. Acad. Sci. USA* 77:4216–4220 (1980).

van Mourik et al., "Vascular Endothelial Cells Synthesize a Plasma Membrane Protein Indistinguishable from the Platelet Membrane Glycoprotein IIa," *J. Biol. Chem.* 260:11300–11306 (1985).

Wilchek et al, "Affinity Chromatography," *Meth. Enzymol.* 104:3–55 (1984).

Williams et al., "The Immunoglobulin Superfamily — Domains for Cell Surface Recognition," *Ann. Rev. Immunol.* 6:381–405 (1988).

Williams, "A Year in the Life of the Immunoglobulin Superfamily," *Immunology Today* 8:298–304 (1987).

Simmons et al. "Molecular cloning of CD31, a putative intercellular adhesion . . . " *J. Exp. Med.*, 171 (6):2147–52 (1990).

Newman et al. "Pecam -1(CD-31) cloning and relation to adhesion molecules of the immunoglobulin gene superfamily," *Science,* 247:1219–1222 (Mar. 9, 1990).

FIG. IA

```
GAATTCCGGGAGAAGTGACCAGAGCAATTTCTGCTTTTCACAGGGCGGGTTTCTCAACGG        60
TGACTTGTGGGCAGTGCCTTCTGCTGAGTCATGCCCGAAGGCAGAACTAACTGTG          120
CCTGCAGTCTTCACTCTCAGGATGCAGCCGAGGTGGGCCCAAGGGCCACGATGTGGCTT      180
                     M  Q  P  R  W  A  Q  G  A  T  M  W  L
                    -27
GGAGTCCTGCTGACCCTTCTGCTCTGTTCAAGCCTTGAGGGTCAAGAAACTCTTTCACA       240
 G  V  L  L  T  L  L  L  C  S  S  L  E  G  Q  E  N  S  F  T        6
ATCAACAGTGTTGACATGAAGAGCCTGCCGGACTGGACGGTGCAAAATGGGAAGAACCTG     300
 I  N  S  V  D  M  K  S  L  P  D  W  T  V  Q  N  G  K  N  L       26
ACCCTGCAGTGCTTCGCCGGATGTCAGCACCTCACGTCAAGCCTCAGCACCAGATG         360
 T  L  Q  C  F  A  D  V  S  T  T  S  H  V  K  P  Q  H  Q  M       46
CTGTTCTATAAGGATGACGTGCTGTTTTACAACATCTCCTCCATGAAGAGCACAGAGAGT    420
 L  F  Y  K  D  D  V  L  F  Y  N  I  S  S  M  K  S  T  E  S       66
TATTTTATTCCTGAAGTCCGGATCTATGACTCAGGAGACATATAAATGTACTGTGATTGTG   480
 Y  F  I  P  E  V  R  I  Y  D  S  G  T  Y  K  C  T  V  I  V       86
AACAACAAAGAGAAAACCACTGCAGAGTACCAGCTGTTGGTTGAAGGAGTGCCCAGTCCC    540
 N  N  K  E  K  T  T  A  E  Y  Q  L  L  V  E  G  V  P  S  P      106
AGGGTGACACTGGACAAGAAAGAGGCCATCCAAGGTGGACATCGTGAGGGTCAACTGTTCT   600
 R  V  T  L  D  K  K  E  A  I  Q  G  G  I  V  R  V  N  C  S      126
GTCCCAGAGGAAAAGGCCCCAATACACTTCACAATTGAAAAACTTGAACTAAATGAAAAA    660
 V  P  E  E  K  A  P  I  H  F  T  I  E  K  L  E  L  N  E  K      146
```

FIG. 1B

```
ATGGTCAAGCTGAAAAGAGAGAAGAATTCTCGAGACCAGAATTTGTGATACTGAATTC    720
 M  V  K  L  K  R  E  K  N  S  R  D  Q  N  F  V  I  L  E  F    166

CCCGTTGAGGAACAGGACCGCGTTTATCCTTCCGATGTCAAGCTAGGATCATTTCTGG    780
 P  V  E  E  Q  D  R  V  L  S  F  R  Q  A  R  I  I  S  G      186

ATCCATATGCAGACCTCAGAATCTACCAAGAGTGAACTGGTCACCGTGACGGAATCCTTC  840
 I  H  M  Q  T  S  E  S  T  K  S  E  L  V  T  V  T  E  S  F    206

TCTACACCCAAGTTCCACATCAGCCCCACCGGAATGATCATGGAAGGAGCTCAGCTCCAC  900
 S  T  P  K  F  H  I  S  P  T  G  M  I  M  E  G  A  Q  L  H    226

ATTAAGTGCACCATTCAAGTGACTCACCTGGCCCAGGAGTTCCAGAAATCATAATTCAG   960
 I  K  T  I  Q  V  T  H  L  A  Q  E  F  P  E  I  I  Q         246

AAGGACAAGGCGATTGTGGCCCACAACAGGCACATGGCAACAAGGCTGTGTACTCAGTCATG 1020
 K  D  K  A  I  V  A  H  N  R  H  G  N  K  A  V  Y  S  V  M    266

GCCATGGTGGAGCACAGTGGCAACTACACAGTGCAAAGTGGAGTCCAGCCGCATATCCAAG 1080
 A  M  V  E  H  S  G  N  Y  T  K  V  E  S  S  R  I  S  K      286

GTCAGCAGCATCGTGGTTAACATCACAGAACTATTTCCAAGCCCGAACTGGAATCTTCC   1140
 V  S  S  I  V  V  N  I  T  E  L  F  S  K  P  E  L  E  S  S    306

TTCACACATCTGGACCAAGGTGAAAGACTGAACCTGTCCTGCCATCCAGGAGCACCT    1200
 F  T  H  L  D  Q  G  E  R  L  N  L  S  S  I  P  G  A  P      326

CCAGCCAACTTCACCATCCAGAAGGAAGATACGATTGTGTCACAGACTCAAGATTCACC   1260
 P  A  N  F  T  I  Q  K  E  D  T  I  V  S  Q  T  Q  D  F  T    346

AAGATAGCCTCAAAGTCGGACAGTGGGACTTATATCTGCACTGCAGTATTGACAAAGTG   1320
 K  I  A  S  K  S  D  S  G  T  Y  I  C  T  A  G  I  D  K  V    366
```

FIG. IC

```
GTCAAGAAAAGCAACACAGTCCAGATAGTCGTATGTGAAATGCTCTCCCAGCCCAGGATT  1380
 V  K  K  S  N  T  V  Q  I  V  V  C  E  M  L  S  Q  P  R  I    386

TCTTATGATGCCCAGTTTGAGGTCATAAAAGGACAGACCATCGAAGTCCGTTGCGAATCG  1440
 S  Y  D  A  Q  F  E  V  I  K  G  Q  T  I  E  V  R ©  E  S     406

ATCAGTGGAACTTGCCTATTCTTACCAACTTTAAAAACAAGTAAAGTTTGGAGAAT      1500
 I  S  G  T  L  P  I  S  Y  Q  L  L  K  T  S  K  V  L  E  N    426

AGTACCAAGAACTCAAATGATCCTGCGGTATTCAAAGACAACCCCACTGAAGACGTCGAA  1560
 S  T  K  N  S  N  D  P  A  V  F  K  D  N  P  T  E  D  V  E    446

TACCAGTGTGTTGCAGATAATTGCCATTCCCATGCCAAAATGTTAAGTGAGGTTCTGAGG  1620
 Y  Q © V  A  D  N  C  H  S  H  A  K  M  L  S  E  V  L  R      466

GTGAAGGTGATAGCCCCGGTTGAGGTCCAGATTTCTATCCTGTCAAGTAAGGTGGTG     1680
 V  K  V  I  A  P  V  D  E  V  Q  I  S  I  L  S  S  K  V  V    486

GAGTCTGGAGAGGACATTGTGCTGCAAGTGCTGTGAATGAAGGATCTGGTCCCATCACC   1740
 E  S  G  E  D  I  V  L  Q © A  V  N  E  G  S  G  P  I  T      506

TATAAGTTTTACAGAGAAAAGAGGGCAAACCCTTCTATCAAATGACTCAAATGCCACC    1800
 Y  K  F  Y  R  E  K  E  G  K  P  F  Y  Q  M  T  S  N  A  T    526

CAGGCATTTTGGACCAAGCAGAAGCAGGAGGAGTATTACTGCACA                 1860
 Q  A  F  W  T  K  Q  K  A  S  K  E  Q  E  G  E  Y  Y © T      546

GCCTTCAACAGCAGCCAACCACGCCTCCAGTGTCCCAGAAGCAAATACTGACAGTCAGA   1920
 A  F  N  R  A  N  H  A  S  S  V  P  R  S  K  I  L  T  V  R    566

GTCATTCTGCCCCATGAAGAAAAGGACTTATTGCAGTGGTTATCATGGAGTGATCATT    1980
 V  I  L  A  P  W  K  K  G  L  I  A  V  V  I  I  G  V  I       586
```

FIG. 1D

```
GCTCTCTTGATCATTGGGCCAAATGTTATTTCTGAGGAAAGCCAAGGCCAAGCAGATG  2040
 A  L  L  I  I  A  A  K  C  Y  F  L  R  R  K  A  K  A  K  Q  M   606
CCAGTGGAAATGTCCAGGCCAGCAGTACCACTTCTGAACTCCAACAACGAGAAATGTCA  2100
 P  V  E  M  S  R  P  A  V  P  L  L  N  S  N  N  E  K  M  S    626
GATCCCAATATGGAAGCTAACAGTCATTACGGTCACAATGACGATGTCAGAAACCATGCA  2160
 D  P  N  M  E  A  N  S  H  Y  G  H  N  D  D  V  R  N  H  A    646
ATGAAACCAATAAATGATAATAAAGAGCCCTGAACTCAGACGTGCAGTACACGGAAGTT  2220
 M  K  P  I  N  D  N  K  E  P  L  N  S  D  V  Q  Y  T  E  V    666
CAAGTGTCCTCAGCTGAGTCTCACAAAGATCTAGGAAAGAAGGACACAGAGACAGTGTAC  2280
 Q  V  S  S  A  E  S  H  K  D  L  G  K  K  D  T  E  T  V  Y  •  686
AGTGAAGTCCGGAAAGCTGTCCCTGATGCCGTGGAAAGCAGATACTCTAGAACGGAAGGC  2340
 S  E  V  R  K  A  V  P  D  A  V  E  S  R  Y  S  R  T  E  G    706
TCCCTTGATGGAACTTAGACACCAAGGCCAGATGCACATCCCTGAAGGACATCCATGTT  2400
 S  L  D  G  T                                                 711
CCGAGAAGAACAGATAATCCCTGTATTTCAAGACCTCTGTGCACTTATTTATGAACCTGC  2460
CCTGCTCCCACAGAACACAGCAATTCCTCAGGCTAAGCTGCCGGTTCTTAAATCCATCCT  2520
GCTAAGTTAATGTTGGGTAGAAAGAGATACAGAGGGG                          2557
```

FIGURE 2

PLATELET CELL ADHESION MOLECULE AND VARIANTS THEREOF

The United States Government has certain rights in the invention described and claimed herein as a result of support, under grants from the United States National Institutes of Health, of work related to said invention.

BACKGROUND OF THE INVENTION

The present invention relates to polypeptide molecules that can act as ligands for proteins and other agents that bind platelet and endothelial cell membranes in vivo.

Cells of many types have surface proteins, called "integrins," that are recognized by extracellular proteins, such as fibronectin, vitronectin, ostopontin, collagens, thrombospondin, fibrinogen and von Willebrand factor (VWF), which affect the attachment of cells to their surroundings. Integrins which act as receptors for several of these extracellular proteins have been identified with human platelet glycoprotein Ib (GPIa), which partially mediates VWF-dependent adhesion of platelets to exposed vascular endothelium; GPIIa, which corresponds to the β chain of the fibronectin receptor; and the heterodimer protein complex GPIIb-GPIIIa, which functions in platelets as a receptor for fibrinogen, for VWF in the absence of fibrinogen, for fibronectin and for vitronectin.

An α-β chain configuration common to GPIIb and GPIIIa is typical of members of the integrin family of receptors. Another group of adhesion-promoting proteins, referred to generically as "cellular adhesion molecules" (CAMs), are classified with proteins encoded by genes of the immunoglobulin gene superfamily. See, e.g., Williams & Barclay, *Ann. Rev. Immunol.* 6: 381–405 (1988), the contents of which are hereby incorporated by reference. Like other proteins associated with the immunoglobulin (Ig) superfamily, CAMs share a common structure—the immunoglobulin homology unit—that is characterized by an amino-acid sequence, approximately 100 residues in length, having a centrally placed disulfide bridge which stabilizes a series of antiparallel β strands into the so-called antibody fold. In particular, the immunoglobulin homology unit comprises a conserved amino-acid sequence Gly-X-X-Val/-Leu/Ile-X-Val/Leu/Ile-X-Cys/(35-55 amino acids)-/Asp-X-Gly-X-Tyr-X-Cys-X-Val/Ala. See Hunkapiller & Hood, *Nature* 323: 15 (1986).

Among the known CAMs are intercellular adhesion molecule-1 (ICAM-1), which mediates leukocyte adhesion by binding the integrin lymphocyte function-associated molecule-1 (LFA-1); carcinoembryonic antigen (CEA); fasciclin II; CD4, a T-cell subset marker which is a component of the cellular receptor for HIV-I; neuronal cell adhesion (N-CAM), which mediates adhesion of neural cells; myelin-associated glycoprotein (MAG), which is understood to function in myelination; lymphocyte function-associated antigen-3 (LFA-3) and the major glycoprotein of peripheral myelin (Po). In addition to the functional association of CD4 with HIV-I, the role of CAMs as viral receptors is reflected in the fact that receptors for two picornaviruses, human rhinovirus and poliovirus have been identified, respectively, with ICAM-1 and a cell surface glycoprotein comprised of three immunoglobulin-like loop domains (compared to five such domains for ICAM-1).

Although CAM molecules fulfill important functions in vivo, no protein obtained in substantially pure form from platelets has ever been identified, structurally or functionally, as a member of the CAM family. A characterization of this sort would be significant because of the role(s) such a protein, and variant molecules based thereon, would be expected to play in basic cell surface recognition events involving platelets, including self-association of platelets (aggregation), with other blood cells and with endothelial cells which line blood vessels; and platelet adhesion to extracellular matrix components, for example, subendothelium exposed in the course of vascular trauma.

SUMMARY OF THE INVENTION

It is therefore an object of the present invention to provide a purified form of a CAM protein, found on platelet and endothelial cells, in amounts which are practicable to recover.

It is also an object of the present invention to provide polypeptide molecules that function, in CAM-like fashion, as receptors for proteins and other agents that bind to platelet membrane proteins in vivo.

It is a further object of the present invention to provide means for producing a protein, possessing the structural attributes associated with the immunoglobulin superfamily, that can be used to influence a platelet-surface recognition event.

In accomplishing the foregoing objects, there has been provided, in accordance with one aspect of the present invention, a composition containing a recoverable amount of PECAM-1. In one preferred embodiment, the composition is PECAM-1 in substantially pure form, while in another preferred embodiment the composition contains is mature PECAM-1.

In accordance with another aspect of the present invention, a PECAM variant has been provided that is selected from the group consisting of a PECAM mutein and a molecule that corresponds to a portion of PECAM-1 or that comprises a portion of PECAM-1 without being coincident therewith, where the molecule displays adhesion-promoting activity. In a preferred embodiment, the PECAM variant corresponds to or comprises an extracellular portion, but not transmembrane portion or an intracellular portion, of PECAM-1. In other preferred embodiments, the aforementioned extracellular portion respectively comprises a N-terminus Gln-Glu-Asn-Ser-Phe and has an amino-acid sequence of 574 residues.

In accordance with yet another aspect of the present invention, a polypeptide molecule has been provided that has an amino-acid sequence which comprises a portion of the PECAM-1 amino-acid sequence, wherein the polypeptide molecule (a) is not coincident with said PECAM-1 amino-acid sequence and (b) possesses PECAM-1 activity. In a preferred embodiment, the polypeptide is between 4 and 100 amino residues long.

Also provided, according to a further aspect of the present invention, are an isolated polynucleotide molecule that encodes PECAM-1 and a polynucleotide molecule that encodes a PECAM variant. In one preferred embodiment, a polynucleotide molecule encodes a protein, preferably having a polypeptide molecular weight of about 79 kilodaltons (kd), with a N-terminus Gln-Glu-Asn-Ser-Phe-Thr-Ile and, moreover, hybridizes under high stringency conditions with an oligonucleotide probe that is complementary to a portion, at least about 10 nucleotides in length, of the nucleotide sequence depicted in FIG. 1.

An oligonucleotide is that additionally provided that corresponds to or is complementary to a portion of a nucleotide sequence depicted in FIG. 1 such that the presence of the oligonucleotide, or a transcription product thereof, in a cell expressing a DNA sequence which encodes PECAM-1 or a PECAM-1 variant, inhibits transcription or translation of the DNA sequence. In preferred embodiments, the oligonucleotide either is RNA (and inhibits translation of the DNA sequence) or is DNA (and inhibits transcription of said DNA sequence).

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description. Unless otherwise indicated, the respective contents of the documents cited below are hereby incorporated by reference.

BRIEF DESCRIPTION OF THE DRAWINGS

FIG. 1A-1D shows the primary structure of a platelet membrane glycoprotein within the present invention (PECAM-1), along with the nucleotide sequence encoding that primary structure. The hydrophobic putative signal peptide and transmembrane domain of the mature glycoprotein are underlined. Two naturally occurring Eco R1 sites are boxed. Cysteine residues, spaced approximately 50 amino acids apart throughout the entire external domain of PECAM-1, are circled; these are thought to participate in disulfide-bond formation within individual immunoglobulin homology units. Predicted glycosylation sites are designated with black triangles. A potential tyrosine phosphorylation site at residue 686 is indicated with a closed circle. The TAG stop codon is underlined in bold.

DETAILED DESCRIPTION OF THE PREFERRED EMBODIMENTS

A platelet membrane glycoprotein has been discovered that is properly characterized as a CAM, according to the criteria discussed above. The mature protein, lacking a 27 amino-acid signal peptide sequence, has a molecular weight of about 130 kilodaltons (kd). Although this size is in the same range as a number of known platelet membrane glycoproteins, the new glycoprotein can be obtained in recoverable amounts, pursuant to the present invention, in a form such that the glycoprotein preparation migrates as a single band on a silver stained SDS-PAGE gel ("substantially pure form"). Preferably, the glycoprotein is in a form of sufficient purity to be usable in therapeutic contexts, including those discussed below.

Figure 1A:
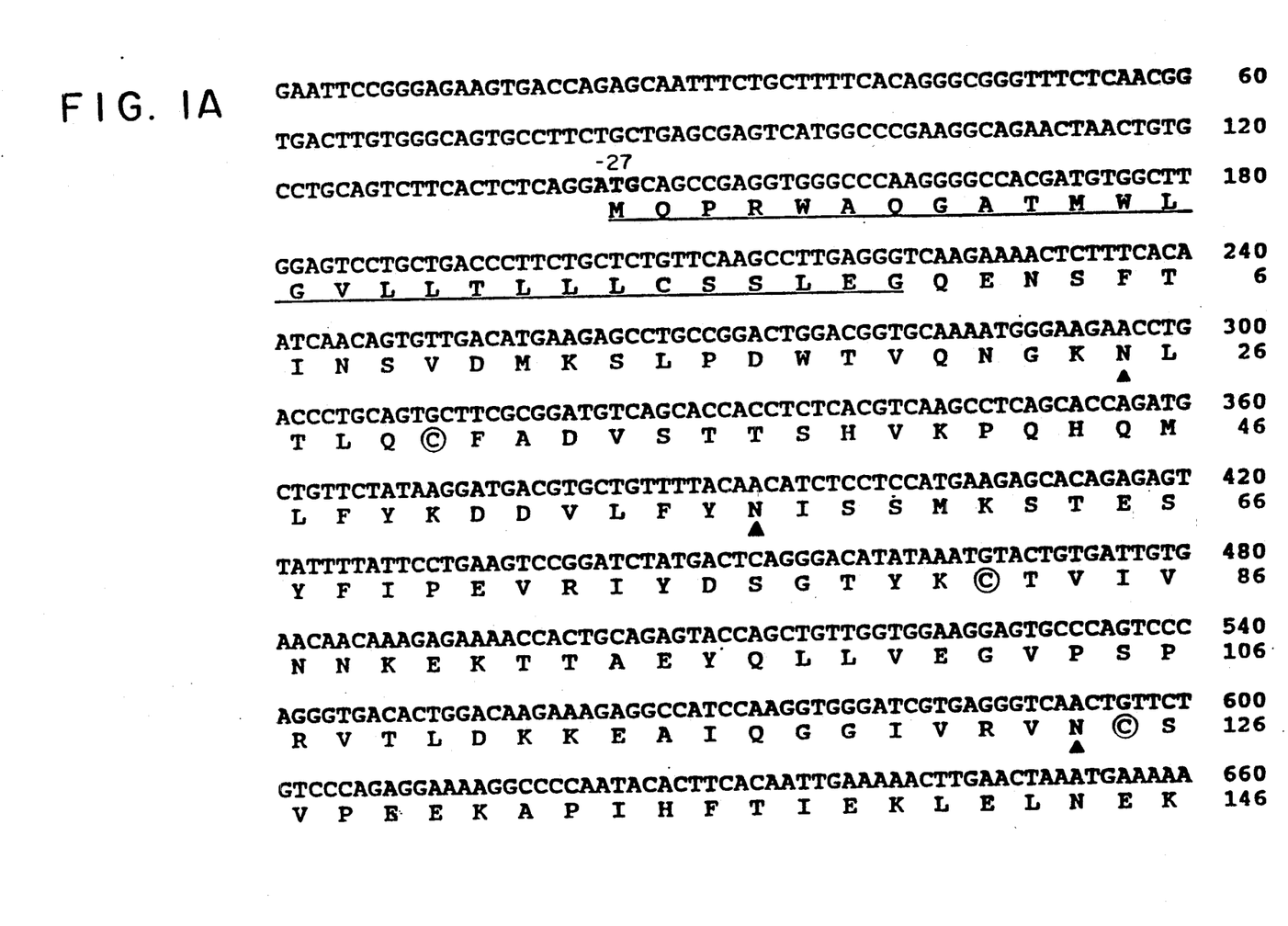
Figure 1B:
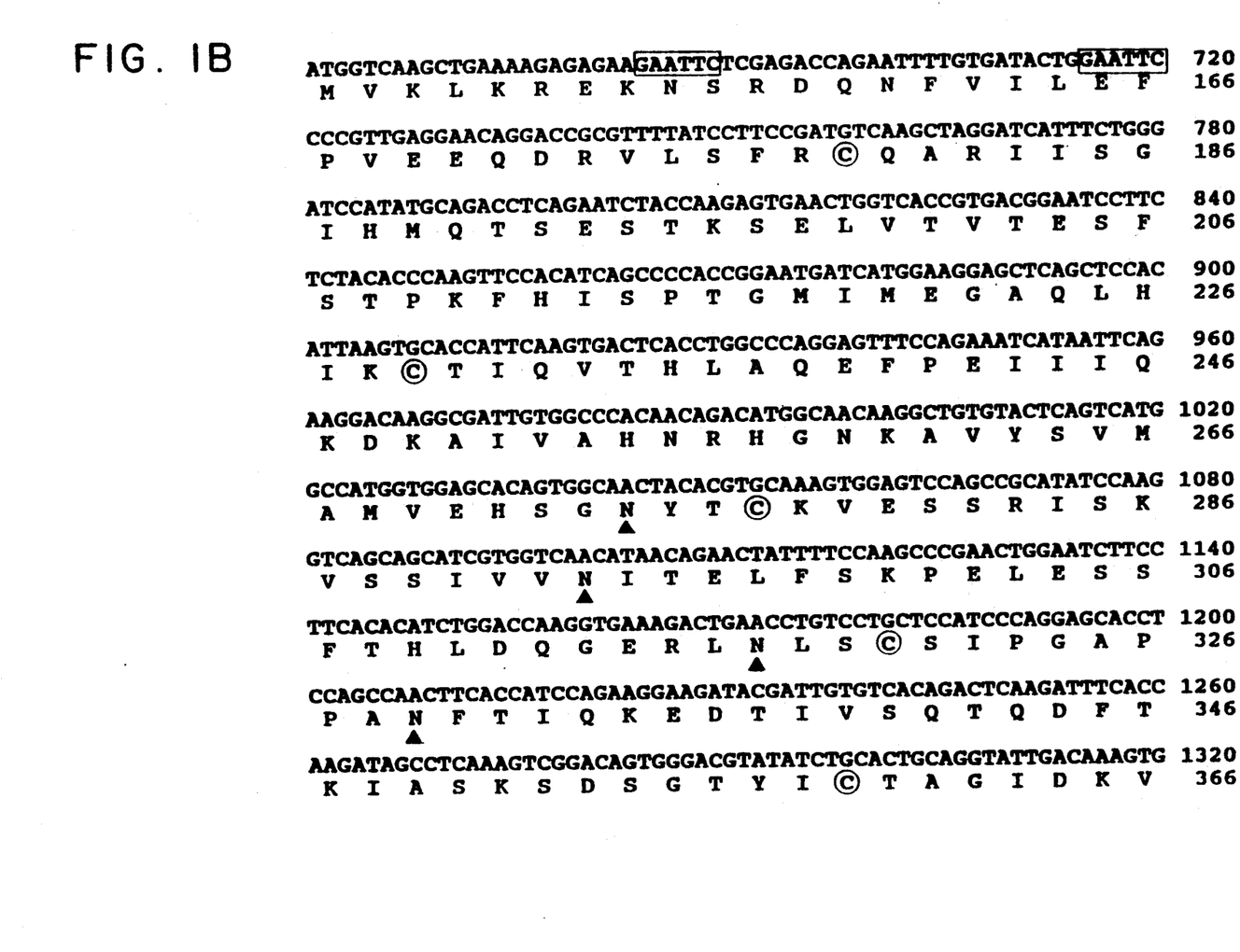
Figure 1C:
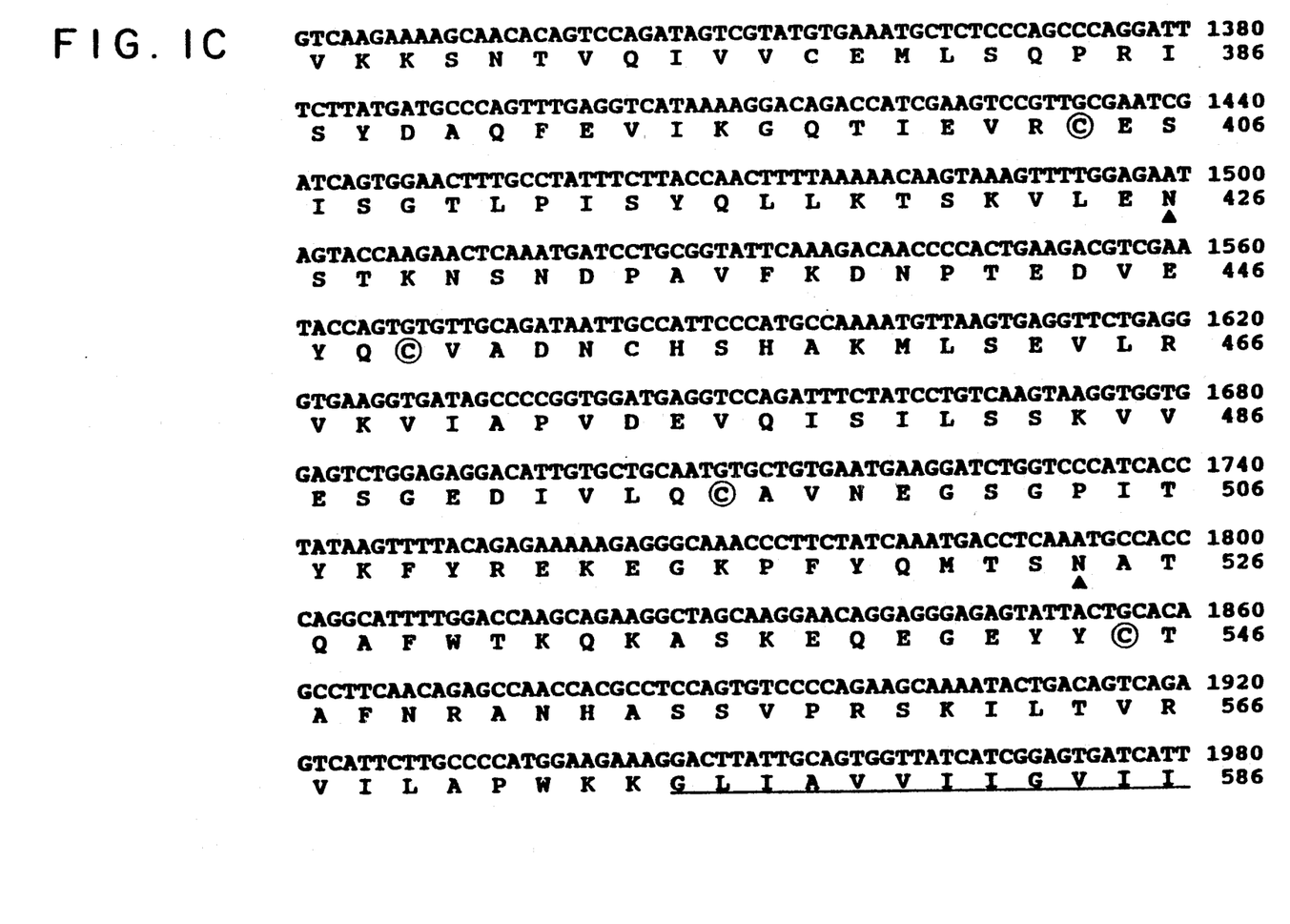
Figure 1D:
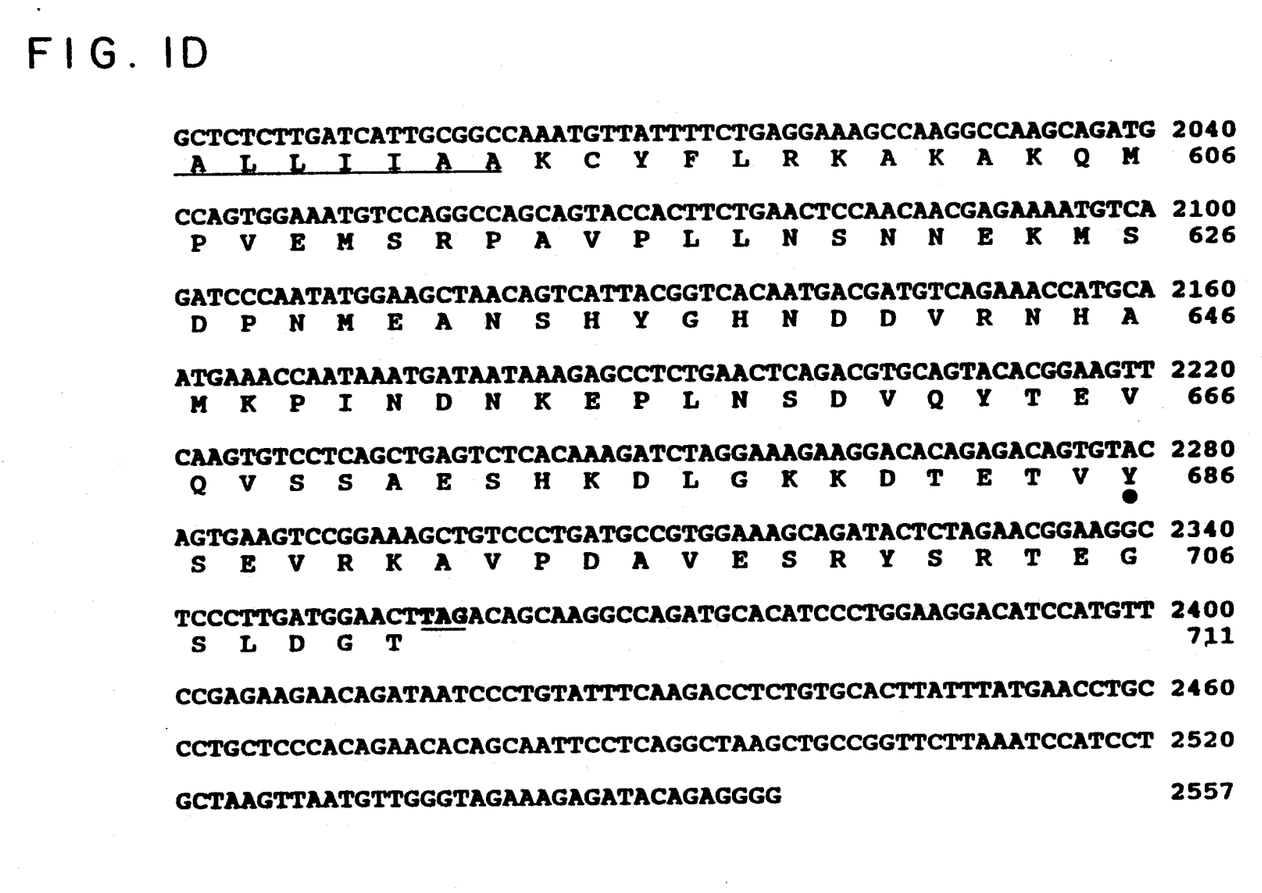
Figure 2:
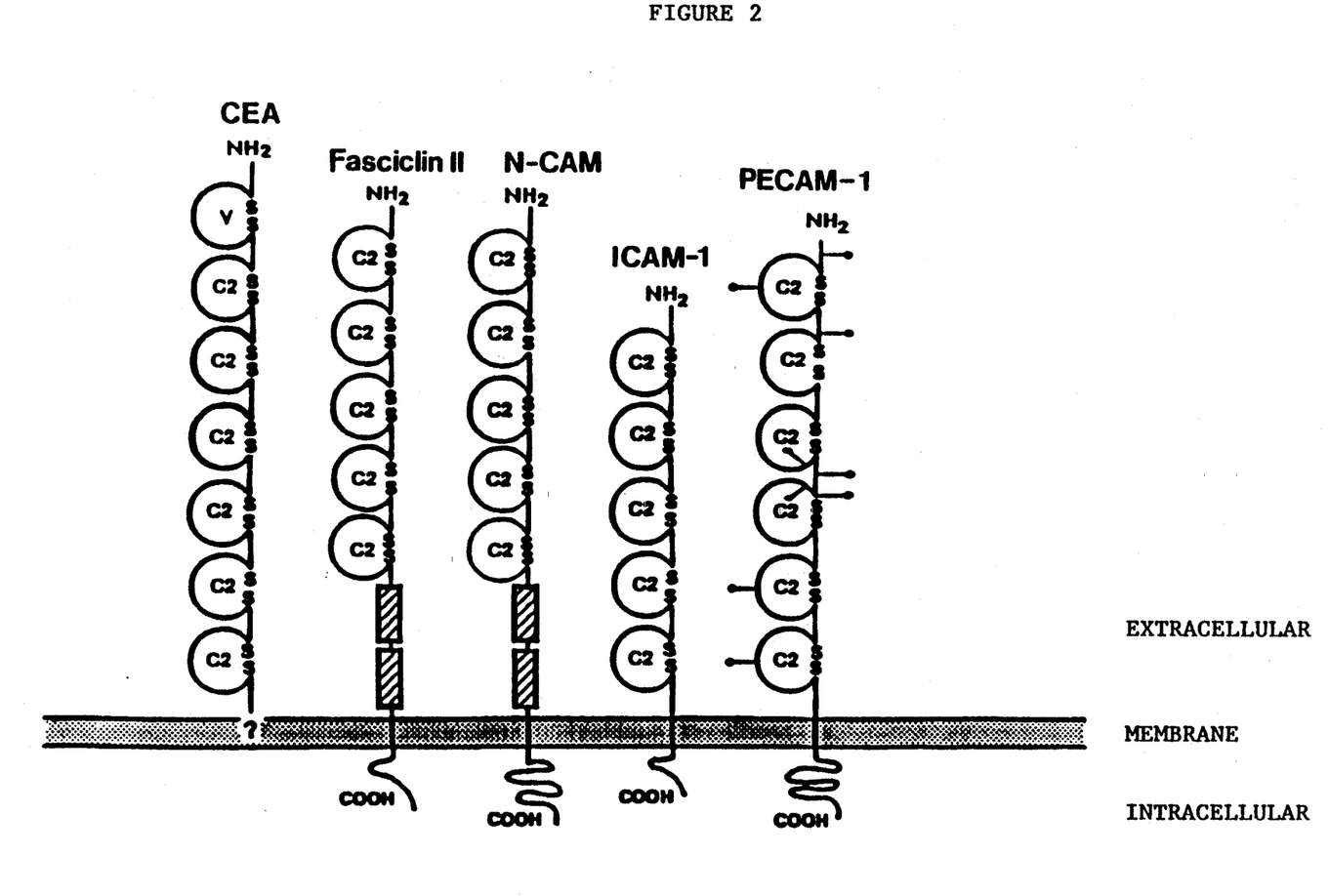
FIG. 2 is a line drawing schematically depicting PECAM-1, along with several other CAM molecules mentioned above, in relation to the cell membrane (stippled region). The circles are representations of individual immunoglobulin homology units. According to the classification of Williams, *Immunology Today* 8: 298 (1987), the depicted CAMs are made up of C2-type domains, with the exception of CEA, which has one V-type domain at the amino terminus. In fasciclin II and N-CAM, the hatched boxes proximal to the membrane represent fibronectin type III domains. Putative N-linked carbohydrate chains on PECAM-1 are symbolized by a (→).

The glycoprotein of the present invention is designated Platelet/Endothelial Cell Adhesion Molecule-1 (PECAM-1) because it is a CAM found on both platelet and endothelial cell membranes. In mature form, PECAM-1 has a 711 amino-acid sequence (polypeptide molecular weight: 79,578 daltons) which is depicted, along with the aforementioned signal peptide, in FIG. 1. PECAM-1 is glycosylated to the extent that approximately 39% of its molecular weight is attributable to carbohydrate, and the mature protein has nine putative, asparagine-linked glucosylation sites, marked by black triangles in FIG. 1. All these sites are present in the glycoprotein extracellular domain, which has 574 amino acids. PECAM-1 also includes a 19 amino-acid transmembrane portion and a 118 amino-acid cytoplasmic domain. This arrangement of domains (see FIG. 2) is consistent with an orientation for PECAM-1, within the plasma membrane, that is typical of other integral membrane glycoproteins.

A polynucleotide that contains a nucleotide sequence encoding PECAM-1 is also shown in FIG. 1. The sequence of 2557 base pairs (bp) contains a 141-bp 5' untranslated (UT) region, a 2214-bp open reading frame which codes for the 738 amino acids that make up the mature protein plus signal peptide, and a 3' UT region of 202 bp. To obtain a polynucleotide which contains a PECAM-1-encoding sequence, it is preferable to use the sequences of the 5' and 3' UT regions to construct complementary oligonucleotide primers, in order to amplify the PECAM-1 coding sequence via polymerase chain reaction (PcR) or similar amplification technique.

PECAM-1 can be found in the membranes of neutrophils, monocytes, bone marrow cells, immature lymphoid cells, myeloid hematopoietic cells and cells from leukemia and lymphoma patients, as well as in platelet and endothelial cell membranes. Substantially pure PECAM-1 can be produced in recoverable amounts by isolating the protein from these cellular sources, and by means of conventional genetic-engineering techniques which are discussed in greater detail below.

A "recoverable" amount in this regard means that the isolated amount of the glycoprotein is detectable by a methodology less sensitive than radiolabeling, such as an immunoassay, and can be subjected to further manipulations involving transfer of the protein per se into solution. Preferably, a recoverable amount of PECAM-1 should be such that transferring the protein into solution yields a concentration of at least 50 nM, and more preferably at least 1 μM.

Isolating recoverable amounts of substantially pure PECAM-1 from natural sources preferably involves the preparation of solubilized membrane proteins from PECAM-1-containing cells, such as platelets, and purification of the mature glycoprotein via immunoaffinity chromatography according to known procedures. See Wilcheck, et al., *Meth. Enzymol.* 104: 3 (1984); and Ausubel, et al. (eds.), CURRENT PROTOCOLS IN MOLECULAR BIOLOGY Wiley Interscience, New York (1987,1989), at Section 10.11. For example, platelets can be isolated, solubilized and centrifuged, followed by application of the resulting supernatant to a lectin-sepharose column, e.g., a Conconavilin A (ConA)-sepharose column. Since PECAM-1 does not bind to ConA-like lectins, the flow-through of such a column can be used to obtain a PECAM-1-enriched preparation.

For further purification, PECAM-1-specific monoclonal antibodies (MAbs) can be attached to an affinity column, such as a sepharose column (see, e.g., Ausubel supra, at Section 10.16), and the flow-through mentioned above can be refluxed through the affinity column to bind PECAM-1. Nonspecific binding can be diminished during the PECAM-1 binding by adjusting pH and salt concentration in the column. Substantially pure PECAM-1 can then be eluted from the column using a suitable acidic elution buffer containing a mild detergent, such as digitonin, octylglucoside, CHAPS or glycine/Triton X-100, and then recovered in useful amounts.

The purity of the PECAM-1 thus obtained can be assessed by running the PECAM-1 preparation on SDS-PAGE, under reducing and nonreducing conditions, to determine whether the PECAM-1 runs as a single band. If necessary, the eluted PECAM-1 can be adsorbed to an additional lectin-sepharose column, such as wheat germ sepharose, and eluted off with a suitable elution buffer, e.g., a glycine buffer containing a mild detergent, to obtain substantially pure PECAM-1.

Antibodies suitable for use in the immunoaffinity-chromatographic purification of PECAM-1 can be obtained as described in greater detail below. It has also been discovered that certain MAbs employed previously in other contexts, such as for distinguishing different stages of lymphoid and myeloid differentiation, can also be used in the immunoaffinity-purification of PECAM-1 according to the present invention. These Mabs include anti-hec7, identified by Muller, et al., *J. Exp. Med.* 170: 399-414 (1989); SG134, disclosed by Goyert, et al., *J. Immunol.* 137: 3909 (1986); CLB-HEC 75, disclosed by van Mourik, et al., *J. Biol. Chem.* 260: 11300 (1985); and TM2 and TM3'identified by Ohto, et al., *Blood* 66: 873 (1985).

As an alternative to immunoaffinity chromatography, conventional glycoprotein purification employing column chromatography can also be employed in isolating PECAM-1 from cellular sources. See Ausubel at Sections 10.12-10.15. A PECAM-1 isolation by this route would involve the use of one or more of ion-exchange high pressure liquid chromatography (HPLC), size-exclusion (SE)-HPLC, high performance chromatofocusing and hydrophobic-interaction chromotography. High performance chromatofocusing and hydrophobic-interaction chromotography would be preferred isolation means since both methods provide rapid purification of biologically active, detergent-soluble proteins like PECAM-1, with minimal denaturation and high recovery.

Based on the nucleotide sequence of FIG. 1 and knowledge of the extracellular, transmembrane and intracellular domains of the mature PECAM-1 molecule (see FIG. 2), polypeptide molecules can also be produced which represent variations of the naturally occurring molecule. These polypeptide molecules are referred to here generically as "PECAM variants" and include, for example, PECAM muteins and molecules that correspond to portions of PECAM-1.

In this regard, a "PECAM mutein" is a polypeptide that retains the basic structural attribute—namely, the immunoglobulin homology unit—and adhesion-promoting activity of a CAM, and that is homologous to PECAM-1. For purposes of this description, "homology" between two sequences connotes a likeness short of identity indicative of a derivation of the first sequence from the second. In particular, a polypeptide is "homologous" to PECAM-1 if a comparison of amino-acid sequences between the polypeptide and PECAM-1, reveals an identity of greater than about 70%. Such a sequence comparison can be performed via known algorithms, such as the one described by Lipman and Pearson, *Science* 227: 1435 (1985), which are readily implemented by computer.

PECAM muteins can be produced, in accordance with the present invention, by conventional site-directed mutagenesis, which is one avenue for routinely identifying residues of the PECAM-1 molecule that can be modified without rendering the resulting polypeptide biologically inactive. See, Ausubel supra, at Section 8. Oligonucleotidedirected mutagenesis, comprising [i] synthesis of an oligonucleotide with a sequence that contains the desired nucleotide substitution (mutation), [ii] hybridizing the oligonucleotide to a template comprising a structural sequence coding for PECAM-1 and [iii] using T4 DNA polymerase to extend the oligonucleotide as a primer, is preferred because of its ready utility in determining the effects of particular changes to the PECAM-1 structural sequence. Its relative expense may militate in favor of an alternative, known direct-mutagenesis method.

Also exemplary of PECAM variants within the present invention are molecules that correspond to a portion of PECAM-1, or that comprise a portion of PECAM-1 without being coincident with the natural molecule, and that display the adhesion-promoting activity of a CAM, as described above. Among these variants would be a polypeptide containing an amino-acid sequence that corresponds to the extracellular domain of PECAM-1, absent the transmembrane or intracellular portions; that is, to a "soluble receptor" form of PECAM-1.

Other PECAM variants of the present invention are fragments of PECAM-1 that retain CAM-like adhesion-promoting activity. Likewise within the present invention would be synthetic polypeptides that (i) correspond to a portion of the PECAM-1 amino-acid sequence and (ii) retain an activity characterisitic of PECAM-1. Such synthetic polypeptides would preferably be between 4 and 100 amino residues in length.

Whether a synthetic polypeptide meeting criterion (i) also satisfies criterion (ii) can be routinely determined by means of an assay for a PECAM-1 activity. Two such activities are the mediation, respectively, of adhesion-dependent movement of cells in response to a chemical attractant (chemotaxis) and of endothelial cell-cell adhesion. The former activity can be assayed, following Ohto, et al., *Blood* 66: 873-81 (1985), by determining whether an antibody that binds the synthetic polypeptide in question also inhibits chemotaxis of neutrophils or monocytes responding to a suitable stimulant, such as *E. coli* endotoxin. The ability to mediate adhesion between endothelial cells can be similarly assayed in routine fashion, i.e., by testing whether a polypeptide-recognizing antibody inhibits the anchoring of dispersed endothelial cells to an suitable substrate and/or the formation thereafter of intercellular junctions.

PECAM variants could be produced by known de Dovo-synthesis techniques and by fragmentation of the PECAM-1 molecule itself, as well as by producing a genetically-engineered host cell that expresses a PECAM fragment encoded by a heterologous polynucleotide used to transform the host. To be used in recombinant expression of a PECAM-1 or a PECAM variant, a polynucleotide molecule encoding PECAM-1 or a PECAM variant would preferably comprise a nucleotide sequence, corresponding to the desired amino-acid sequence, that is optimized for the host of choice (see below) in terms of codon usage, initiation of translation, most suitable glycosylation, and expression of commercially useful amounts of PECAM-1 or a desired PECAM variant. Also, the vector selected for transforming the chosen host organism with such a polynucleotide molecule should allow for efficient maintenance and transcription of the sequence encoding the polypeptide.

Preferred among the hosts generally available for transformation, pursuant to the present invention, are eukaryotes capable of effecting glycosylation at sites identified in FIG. 1. These eukaryotes are exemplified by yeast expression systems, including those employing species of Saccharomyces, Pichia and Kluyveromyces, respectively. See, for example, U.S. Pat. Nos. 4,456,082 and 4,837,147 (Saccharomyces); U.S. Pat. Nos. 4,855,231, 4,808,537 and 4,857,467 (Pichia); and U.S. Pat. Nos. 4,806,472 and 4,859,596 (Kluyveromyces).

The choice of an appropriate yeast strain for transformation will be determined in large part by the selectable marker(s) and other features of the vector employed. In addition, since a recombinant PECAM molecule slated for therapeutic application may elicit an allergic reaction to host-related carbohydrate moieties with which the molecule is glycosylated, it may prove advantageous to select a host for the ability to produce a heterologous PECAM protein having reduced glycosylation. Once such a PECAM-producing host cell has been selected, then specific clones can be screened to select for variations in glycolsylation pattern that are most suitable for a therapeutic application. Yeast strains which are exemplary of those suitable for use according to the present invention are strain X2181-1B, with genotype α trpl gall adel his2 (available from the Yeast Genetic Stock Center, Berkeley, Calif.; strain ATCC 52683, with genotype αhis2 adel trpl metl4 ura 3 (aka strain "J17," available from the American Type Culture Collection, Rockville, Md.); and strain ATCC 46183, with genotype α hisl trpl (aka "strain IL166-5B," also available for the American Type Culture Collection).

Another type of preferred expression system entails the use of a mammalian host cells transformed with a polynucleotide within the present invention. Illustrative of suitable mammalian-cellular hosts which can be used for this purpose are Chinese ovary (CHO) cells as described by Urlaub & Chasin, *Proc. Nat'l Acad. Sci. USA* 77: 4216 (1980); baby hamster kidney (BHK) cells, exemplified by a cell line deposited under accession number ATCC CCL 10 and another line ATCC CCL 70; monkey kidney CVI cells transformed with SV40, exemplified by a line deposited under accession number ATCC CRL 1651 (aka "COS-7"); human embryonic kidney cells of the sort represented in a cell line described by Graham, et al., *J. Gen. Virol.* 36: 59 (1977); mouse sertoli cells as described by Mather, *Biol. Reprod.* 23: 243-51 (1980); african green monkey kidney cells as exemplified by line ATCC CRL 1587 (aka "VERO-76"); human cervical carcinoma (HELA) cells (see, e.g., line ATCC CCL 2); canine kidney cells of the sort deposited under ATCC 34 (aka "MDCK"); buffalo rat liver cells as exemplified by line ATCC CRL 1442 (aka "BRL 3A"); human lung cells such as are represented by line ATCC CCL 75 (aka "W138"); human liver cells (see, e.g., Hep G2, HB 8065); mouse mammary tumor cells of the sort deposited under ATCC CCL 51 "MMT 060562"); and TRI cells as described by Mather, et al., *Ann. N.Y. Acad. Sci.* 383: 44 (1982).

For both yeast and mammalian expression systems, there are conventional transformation and screening protocols which can be employed pursuant to the present invention. Standard methodology in this regard is detailed in CURRENT PROTOCOLS IN MOLECULAR BIOLOGY, Chapter 9 (mammalian cells) and Chapter 13 (yeast cells), loc. cit. For example, transformants can be selected for expression of functional PECAM-1 or a PECAM variant by use of MAbs which display an appropriate PECAM specificity, as described above.

For introducing a polynucleotide of the present invention into a yeast cell, the most commonly used protocol, the lithium acetate method, exploits the fact that alkali cations make yeast cell membrane permeable to DNA; in addition, uptake of foreign DNA is promoted by the presence in the medium of a high-molecular-weight molecule, polyethylene glycol. An alternative method, spheroplast transformation, can be used but is more time-consuming than the lithium acetate procedure but results in a higher efficiency of transformation per input DNA.

Introduction of a polynucleotide of the present invention into mammalian cells to produce a recombinant cell which expresses PECAM-1 or a PECAM variant can be accomplished according to conventional procedures, such as by calcium phosphate or DEAE-dextrane transfection. See, e.g., Ausubel supra, at Chapter 9. Expression of such recombinant cells of the present invention provides recoverable amounts of a PECAM-1 or a PECAM variant.

As discussed below, PECAM-1 is at least immunologically related to an antigen, designated "CD31," that has been characterized serologically by Lee, et al., *J. Exp. Med.* 168: 1193-98 (1988), but never provided in recoverable form. CD31 displays differential expression in various types of leukemia and, hence, can be used as a indicator of leukemia type. PECAM-1 should likewise be useful as a leukemia indicator, and labeled oligonucleotide probes ("PECAM probes") can be designed, based on a polynucleotide encoding PECAM-1 or a PECAM variant, that should find use in the classification of various leukemic states.

A PECAM probe of this sort can be a fragment of an oligonucleotide that is complementary to a polynucleotide encoding PECAM-1 or a PECAM variant. Alternatively, a synthetic oligonucleotide can be used as a PECAM probe which is preferably at least about ten nucleotides in length, in order to be specific for a PECAM-1- or PECAM variant-encoding polynucleotide. Nucleic acids can be isolated from the blood of a patient or from a tissue biopsy and analyzed by hybridization to labeled PECAM probes. Such probes preferably hybridize to PECAM-1-encoding nucleotides under high stringency conditions, i.e., under hybridization and washing conditions (buffer ionic strength, temperature, duration, etc.) such that nonspecific binding of a probe is minimized. For probe design, hybridization technique and stringency conditions, see Ausubel supra, sections 6.3 and 6.4. Additional approaches to probe design and detection can also be used, e.g., ligase-mediated gene detection (LMGD), as disclosed by Landegren, et al., *Science* 241: 1077-80 (1988) and fluorescence resonance energy transfer (FRET), as disclosed by Wolf, et al, *Proc. Nat'l Acad. Sci. USA* 85: 8790-94 (1988).

PECAM-1 is also believed to play a role in chemotaxis by neutrophil cells and in the formation of endothelial-cell intercellular junctions. PECAM-1 or a PECAM variant, especially the soluble-receptor form described above, should therefore prove useful in modulating angiogenic processes which depend on neutrophil chemotaxis and/or formation of junctions between endothelial cells, for example, in tumor development.

In a related vein, so-called "antisense" oligonucleotides can be prepared as polynucleotides complementary to (a) nucleotide sequences comprising a DNA which codes for PECAM-1 or a PECAM variant or (b) nucleotide sequences comprising PECAM-1 or PECAM variant messenger RNA (mRNA). For both types, the length of an antisense oligonucleotide of the present invention is not critical so long as there is no promoter sequence (for DNA) or Shine-Delgarno site (for RNA) present. Type (a) antisense oligonucleotides would be synthesized de novo, for example, based on knowledge concerning the nucleotide sequence of the cDNA insert shown in FIG. 1. Type (b) antisense oligonucleotides could also be produced Dovo (DNA or RNA) or by transforming an appropriate host organism with DNA that is transcribed constitutively into RNA which binds a PECAM-1 or PECAM variant mRNA. Both type (a) and type (b) oligonucleotides within the present invention are expected to be useful as agents for "down-regulating" (turning off) the expression of PECAM-1 on the cell surface, or inhibiting either transcription [type (a)] or translation [type (b)].

PECAM-1 and PECAM variants, or antibodies raised against one or more of these polypeptides, are expected to have a utility in the prevention of metastatic disease. In this context, the term "antibody" encompasses monoclonal and polyclonal antibodies. Such an antibody can belong to any antibody class (IgG, IgM, IgA, etc.). For monoclonal antibody (Mab) production, one generally proceeds by isolating lymphocytes and fusing them with myeloma cells, producing hybridomas. The cloned hybridomas are then screened for production of "anti-PECAM" antibodies, i.e., antibodies that bind preferentially to either PECAM-1 (full-length or mature form) or a PECAM variant. "Antibody" also encompasses fragments, like Fab and F(ab')$_2$, of anti-PECAM antibodies, and conjugates of such fragments, and so-called "antigen binding proteins" (single-chain antibodies) which are based on anti-PECAM antibodies, in accordance, for example, with U.S. Pat. No. 4,704,692.

Alternatively, Mabs or a fragment thereof within the present invention can be produced using conventional procedures via the expression of isolated DNA which codes for variable regions of such an Mab in host cells like *E. coli,* see Ward, et al., *Nature* 341: 544-46 (1989), or transfected murine myeloma cells, see Gillies, et al., *Biotechnol.* 7: 799-804 (1989), and Nakatani, et al., loc. cit., 805-10. In addition, Fab molecules can be expressed and assembled in a genetically transformed host like *E. coli.* A lambda vector system is available thus to express a population of Fab's with a potential diversity equal to or exceeding that of subject generating the predecessor antibody. See Huse, et al., *Science* 246: 1275-81 (1989).

Antibodies against PECAM-1 or a PECAM variant can also be employed in the generation, via conventional methodology, of anti-idiotypic antibodies (antibodies that bind an anti-PECAM antibody), e.g., by the use of hybridomas as described above. See, for example, U.S. Pat. No. 4,699,880. Such anti-idiotypic antibodies could be used to sequester anti-PECAM antibodies in an individual, thereby to treat or prevent pathological conditions which may be associated with an immune response whereby PECAM-1 is recognized as "foreign" by the immune system of the individual.

The present invention is further described by reference to the following, illustrative examples.

EXAMPLE 1

Preparation of Enriched Lysate Containing PECAM-1, and Generation of Multispecific Polyclonal Antibodies to Platelet Membrane Proteins A lysate enriched for human platelet integral membrane proteins was prepared in accordance with Newman, et al., *Thrombosis Res.* 27: 221-24 (1982), and multispecific polyclonal antibody directed against the lysate was prepared, following Newman, et al., *J. Cell Biol.* 103: 81-86 (1986). Thus, platelet concentrates were obtained by differential centrifugation of units of whole human blood, and platelet membranes were prepared from the concentrates by sonication and differential centrifugation. See Newman, et al., *J. Cell Biol.* 90: 249-53 (1981). One unit of platelet concentrate yielding a membrane pellet which contained 5-8 mg of protein. The pellet was dissolved in 2 ml of 1% Triton X-114 (Sigma Chemical Company, St. Louis, Mo.) in 10 mM Tris, 150 mM NaCl (pH 7.4), which contained both 0.4 mM phenylmethylsulfonyl fluoride and 5 mM EDTA as protease inhibitors. After brief sonication to disperse membrane aggregates, solubilization was carried out on ice for 60 minutes.

The Triton-solubilized membranes were then centrifuged at 100,000 $\times$g for 60 minutes, and 200 $\mu$l of the supernatant carefully applied to the top of a 300 $\mu$l of 6% sucrose cushion in a 1-ml polystyrene Fisher centrifuge tube (Fisher Model 59 microcentrifuge). The tube was warmed above the cloud point of the detergent by incubation for five minutes at 37° C., and then centrifuged for five minutes at 1500 $\times$g to pellet the large protein-detergent mixed micelle aggregates which formed. The aqueous phase, which remained on top of the sucrose cushion, was removed, cooled to 0° C. and re-extracted by the addition of ice-cold Triton X-114 to a final concentration of 1%. This solution was again warmed, loaded back on top of the 6% sucrose cushion, and centrifuged as above. The detergent phase was recovered as a yellowish oily droplet beneath the sucrose cushion.

Both the detergent and aqueous phases were first assayed for protein concentration (3) and then diluted 1:1 with SDS solubilization solution (4% SDS, 100 mM Tris-HCl, pH 6.8, 10% glycerol, 0.001% bromphenol blue) prior to analysis by SDS-polyacrylamide gel electrophoresis. For reduced samples, 2-mercaptoethanol was added to a final concentration of 5%. After boiling the samples for five minutes, 5-50 ug/well of protein was applied to a 7% SDS polyacrylamide slab gel and electrophoresed for approximately 3 hours at 30 mA. After electrophoresis, gels were fixed and silver stained according to the method of Merril, et al., *Science* 211:1437-38 (1981).

The polyclonal antiserum was prepared in rabbits by twice-monthly intradermal injection of the enriched lysate described above. Purified IgG was obtained using a conventional combination of ammonium sulfate fractionation and DEAE cellulose chromatography. The specificity of the resulting preparation was confirmed by immunoprecipitation of radioiodinated, solubilized platelets, by crossed immunoelectrophoresis vs. solubilized whole platelets, and by western blot analysis, according to known methods. See, e.g., Ausubel supra, at Section 10.

EXAMPLE 2

Antibody Screening of cDNA Library for PECAM-1-Encoding Clones, and Epitope Selection of PECAM-1-Specific Antibody The polyclonal antiserum thus prepared was then used to screen an cDNA λgt11 expression library made from the permanent endothelial cell/lung carcinoma hybrid cell line, EA.hy 296, described by dgel, et al., *Proc. Nat'l Acad. Sci. USA* 80: 3734 (1983). In particular, the identities of antibody-positive clones were determined using the "epitope selection" method disclosed, e.g., by Hall, et al., *Nature* (London) 311: 379 (1984), in which immobilized β-galactosidase fusion proteins from plaque-purified, antibody-positive clones were used to select from the polyspecific antiserium those antibodies capable of binding specific epitopes encoded by each fusion protein.

By this approach two clones, 8B and 8C, were identified that selected antibodies reacting on immunoblots with a single, 130-kd platelet protein. To isolate the 130-kd protein from the known platelet membrane glycoproteins in the same molecular-weight range, two-dimensional nonreduced/reduced gel electrophoresis was employed to permit accurate characterization of the protein encoded by clones 8B and 8C.

More specifically, the λgt11 bacteriophage clone 8B, containing a 1.6 kb insert, was grown on a lawn of *E. coli* strain 1090 to a density of approximately 50,000 pfu/plate and induced for expression of its β-galactosidase fusion protein with isopropylthiogalactoside. The plate was overlayed with a 150 mm nitrocellulose circle for 3 hours to adsorb the induced phage proteins. After blocking unbound sites with gelatin, the nitrocellulose membrane was incubated with a polyclonal rabbit antiserum raised against human platelet integral membrane proteins, thereby allowing the antibody population specific for the expressed epitopes to specifically bind to the immobilized fusion protein. After extensive washing, the epitope-selected antibody, ES8B, was eluted from the membrane with pH 2.3 glycine-HCl, neutralized with Tris base, and reacted with a western blot of whole platelet lysates to demonstrate a specificity by the antibody for the unique protein spot representing the 130-kd platelet protein. Binding was visualized by means of an alkaline phosphatase-conjugated second antibody followed by a 5-bromo-4-chloro-3-indolyl phosphate/nitro blue tetrazolium salt substrate pair.

EXAMPLE 3

PECAM-1 Characterization and Binding by Epitope-Selected Antibody

The epitope-selected antibody from clone 8B thus reacted on western blot with PECAM-1 as a single protein spot that was distinct from other platelet membrane proteins, including GPIa, GPIIa, GPIIb and GPIIIa. The protein distinguished in this manner, PECAM-1, migrated slightly above a diagonal line formed by proteins for which electrophoretic migration is unaffected by reducing agents, indicating that the isolated protein is a single-chain protein containing intrachain disulfide bonds.

Various biochemical criteria found applicable to PECAM-1 are consistent with a protein that is a highly glycosylated, major surface membrane glycoprotein. Thus, treatment of intact platelets with trypsin, neuraminidase and N-glycanase, respectively, caused a marked reduction in the molecular weight of isolated PECAM-1 polypeptide, as assessed by western blot analysis of subsequently washed and detergent-lysed platelets. This reduction in molecular weight indicated that glycosylation of PECAM-1 was significant and that the protein portion contained exposed amino-acid sequences that were susceptible to trypsin hydrolysis. PECAM-1 was labeled effectively by treatment of intact platelets with periodate/sodium boro[$^3$H] hydride, a carbohydrate-specific label, and less so by lactoperoxidase-catalyzed surface radioiodination. Semiquantitative, comparative western blot analysis, effected by means of antibody probes to a number of different, well-characterized platelet membrane glycoproteins indicated that PECAM-1 is a major membrane component. That PECAM-1 stains only weakly with Coomassie blue accounts for its not having been isolated and characterized previously.

A series of monoclonal antibodies previously raised against platelet and endothelial cell surface glycoproteins similar in size and pI to PECAM-1 were tested for their ability to react with the latter molecule. Two of these monoclonal antibodies, anti-CD31 and anti-hec7, reacted with a platelet protein the co-migrated on SDS-PAGE gels with PECAM-1, As previously mentioned, CD31 is a leukocyte differentiation antigen of uncharacterized structure and function which has been reported to be present on (but has never been obtained in recoverable amounts from) human platelets, endothelial cells, granulocytes and monocytes. See Knapp, et al., *Immunology Today* 10: 253 (1989). The hec7 antigen, which has also not been isolated in recoverable amounts, is reported to be localized to the intercellular junctions of human endothelium. Muller, et al., *J. Exp. Med.* 170: 399 (1989).

Preparations containing the hec7 and CD31 antigens were prepared, via immunoprecipitation with their respective monoclonal antibodies, from human endothelial cell lysates. (MAbs provided by Dr. William A. Muller (Rockefeller University) and Dr. Sanna M. Goyert (Cornell University).) Analysis of the preparations by immunoblotting with an anti-PECAM antiserum indicated that PECAM-1, the CD31 antigen and the hec7 antigen are at least immunologically related.

EXAMPLE 4

Determination of a Nucleotide Sequence Coding for PECAM-1

The 1.6kb cDNA insert from clone 8B was subcloned into a pUC18-derived plasmid vector, pTZ18r. The 8B insert was then used as a probe according to known procedures, as disclosed, for example, by Ausubel supra, at Section 6.3, to identify twenty-three additional clones which were subsequently characterized by restriction mapping and hybridization analysis according to known methods. Two of these clones, 6-4 (spanning nucleotide 1 to about nucleotide 1170 in FIG. 1) and 6-2 (from nucleotide 715 to nucleotide 2557), were found to overlap and contain the entire PECAM-1 encoding sequence, depicted in FIG. 1.

As mentioned above, the 2557-bp PECAM-1 sequence includes a 141-bp 5' untranslated (UT) region and a 3' UT region of 202 bp, in addition to the 2214-bp coding sequence for the mature protein plus signal peptide. The 5' UT region contains two eukaryotic initiation (AUG) codons, beginning at base 95 and nucleotide 142, respectively. Both of these codons are flanked by nucleotides, constituting a "Kozak sequence" that should accommodate initiation of protein synthesis by virtue of its being largely devoid of T residues and having a purine at the −3 position See Kozak, et al., *Nucleic Acids Res.* 15: 8125 (1987).

As is true for many upstream initiation codons lying within a Kozak sequence, the ATG at base 95 of the PECAM-1-encoding nucleotide sequence is followed by a TAA stop codon only 15 bases downstream. This arrangement indicates that translation likely is effected for the 15-bp "minicistron" and then is terminated, after which ribosomes re-initiate translation at base 142 and continue until the stop codon at base 2356.

EXAMPLE 5

Purification of PECAM-1 from a Natural Source

Recoverable amounts of substantially pure PECAM-1 were isolated from blood platelets as follows. Platelets were prepared from whole blood by differential centrifugation according to conventional procedures. Platelets were washed several times in TBS (20 mM TRIS, 150 mM NaCl, 1 mM EDTA, pH 7.4) and then solubilized in TBS containing 1% Triton X-100 and 1 mM $CaCl_2$ in the presence of protease inhibitors (0.4 mM phenylmethylsulfonyl chloride, 10 μM leupeptin). The mixture was next clarified by centrifugation at 15,000g for 30 minutes, and the supernatant was then added to a column of Conconavilin A sepharose to remove any other glycoproteins. The flow-through of this column was applied to an immunoaffinity column specific for PECAM-1, using anti-hec7 antibody attached to a sepharose column. PECAM-1 was then eluted by a brief pulse of a solution containing 100mM glycine/HCL and 0.1% Triton X-100 at pH 2.4. The eluate was neutralized with TRIS base and analyzed by SDS-PAGE to establish purity. If further purification was necessary, then the eluate was adsorbed to a wheat germ sepharose column and eluted off with 0.3M N-acetylglucosamine. Thus, PECAM-1 was obtained, in recoverable amounts, in a preparation that ran as a single band on both a reducing and a non-reducing SDS-PAGE gel.

What is claimed is:

1. A composition containing at least 50 nM of substantially purified PECAM-1, wherein said PECAM-1 is mature PECAM-1 and consists of the amino acid sequence 1-711 of FIG. 1.

2. A PECAM molecule which consists of a portion of the amino acid sequence 1-711 of PECAM-1 of FIG. 1, wherein said molecule corresponds to or comprises an extracellular portion, but not a transmembrane portion or an intracellular portion, of PECAM-1.

3. A PECAM variant according to claim 2, wherein said extracellular portion comprises a N-terminus Gln-Glu-Asn-Ser-Phe.

4. A PECAM molecule according to claim 2, wherein said extracellular portion has an amino-acid sequence corresponding to amino-acids 1-574 in FIG. 1.

* * * * *

UNITED STATES PATENT AND TRADEMARK OFFICE
CERTIFICATE OF CORRECTION

PATENT NO. : 5,264,554

DATED : November 23, 1993

INVENTOR(S) : Peter J. Newman

It is certified that error appears in the above-indentified patent and that said Letters Patent is hereby corrected as shown below:

Column 3, Line 54, of the Patent, "(→)." should be
--(→).--

Column 5, Line 42, of the Patent, "Ausubel at Section" should be --Ausubel supra, at Section--.

Column 6, Line 16, of the Patent, "Oligonucleotidedirected" should be --Oligonucleotide-directed--.

Column 6, Lines 63 and 64, of the Patent, "de Dovo-syntheses" should be --de novo synthesis--.

Column 8, Line 2, of the Patent, "51 "MMT" should be --51 (aka "MMT--.

Column 9, Line 24, of the Patent, "Dovo" should be --de novo--.

UNITED STATES PATENT AND TRADEMARK OFFICE
CERTIFICATE OF CORRECTION

PATENT NO. : 5,264,554
DATED : Nov. 23, 1993
INVENTOR(S) : Peter J. Newman

It is certified that error appears in the above-indentified patent and that said Letters Patent is hereby corrected as shown below:

Column 11, line 17, "dgel," should read --Edgel,--.

Signed and Sealed this

Fourteenth Day of June, 1994

Attest:

BRUCE LEHMAN

Attesting Officer     *Commissioner of Patents and Trademarks*